United States Patent [19]

Standen

[11] Patent Number: 5,360,919
[45] Date of Patent: Nov. 1, 1994

[54] POLYCYCLIC DYES

[75] Inventor: Michael C. H. Standen, Auchterarder, Scotland

[73] Assignee: Zeneca Limited, London, England

[21] Appl. No.: 28,695

[22] Filed: Mar. 8, 1993

[30] Foreign Application Priority Data

Mar. 9, 1992 [GB] United Kingdom ............ 9205049.1

[51] Int. Cl.$^5$ ............................................ C07D 57/00
[52] U.S. Cl. ................................. 549/299; 549/304; 549/305
[58] Field of Search .................... 549/299, 304, 305

[56] References Cited

U.S. PATENT DOCUMENTS 4,859,700 8/1989 Lavielle et al. ................. 549/305 X

FOREIGN PATENT DOCUMENTS 0252406 1/1988 European Pat. Off. .
0363034 4/1990 European Pat. Off. .
2235728 1/1975 France .

Primary Examiner—Johann Richter
Assistant Examiner—Catherine S. Kilby Scalzo
Attorney, Agent, or Firm—Cushman, Darby & Cushman

[57] ABSTRACT

A process for the preparation of a compound of Formula (1):

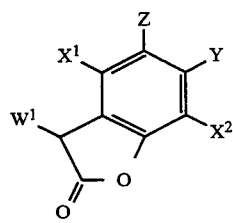

Formula (1)

wherein:
$W^1$ is aryl;
$X^1$ and $X^2$ are each independently selected from —H, —CN, halogen, alkyl, aryl and —COOH;
Y is —H;
Z is —OH; or
Y and Z together form a group of Formula (2):

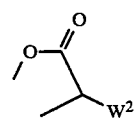

Formula (2)

wherein:
$W^2$ is aryl;
which comprises reacting a compound of Formula (3):

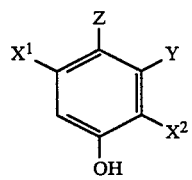

Formula (3)

wherein:
$X^1$, $X^2$, Y and Z are as hereinbefore defined with a compound of Formula (4):

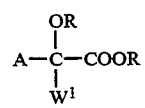

Formula (4)

wherein the substituents are as defined in the specification.

7 Claims, No Drawings

POLYCYCLIC DYES

The present invention relates to a process for the preparation of polycyclic dyes.

Processes for the preparation of polycyclic dyes are known where quinones or hydroquinones are reacted with a variety of substituted acetic acids firstly to form a benzofuranone and secondly by reaction with a further substituted acetic acid to form a benzodifuranone. The first and second stages are catalysed by the addition of acetic, propionic or butyric acids (EP 0 363 034A) or sulphuric acid (GB 1568231) or p-toluenesulphonic acid (EP 0 146 269A).

Polycyclic dyes made using processes which incorporate these acid catalysts suffer from a number of disadvantages in that product yields are generally significantly less than 50%, product physical form is fine giving rise to problems with filtration during isolation of the products and recovery of solvents is hampered by reaction mixtures becoming immobile as reaction solvents are removed.

The present invention seeks to overcome the above problems by providing an improved catalyst for use in the preparation of polycyclic dyes.

According to the present invention there is provided a process for the preparation of a compound of Formula (1):

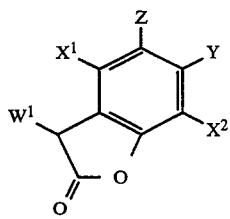

Formula (1)

wherein:

$W^1$ is aryl;

$X^1$ and $X^2$ are each independently selected from —H, —CN, halogen, alkyl, aryl and —COOH;

Y is —H:

Z is —OH; or

Y and Z together form a group of Formula (2):

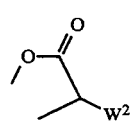

Formula (2)

wherein:

$W^2$ is aryl;

which comprises reacting a compound of Formula (3):

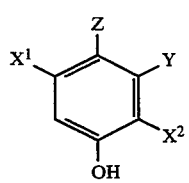

Formula (3)

wherein:

$X^1$, $X^2$, Y and Z are as hereinbefore defined with a compound of Formula (4):

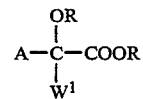

Formula (4)

wherein:

R is —H or -alkyl;

A is selected from —H, —COOR, —OR and aryl in which R is as hereinbefore defined; and $W^1$ and $W^2$ are as hereinbefore defined, in the presence of an acid catalyst characterised in that the catalyst is a long chain alkyl- or long chain alkylaryl-sulphonic, disulphonic or phosphonic acid.

The long chain alkyl group in the long chain alkylsulphonic, disulphonic and phosphonic acid catalyst is preferably a $C_{6-25}$-alkyl group, more preferably a $C_{6-20}$-alkyl group and especially a $C_{8-16}$-alkyl group. The long chain alkylaryl group in the long chain alkylarylsulphonic, disulphonic and phosphonic acid catalyst is preferably a $C_{6-25}$-alkylphenyl group, more preferably a $C_{6-20}$-alkylphenyl group and especially a $C_{8-16}$-alkylphenyl group. In the alkylphenyl sulphonic and phosphonic acid catalyst the alkyl group is preferably in the 4-position of the phenyl ring with respect to the sulphonic or phosphonic acid group. In the alkylphenyl disulphonic acid catalyst the alkyl group is preferably in the 4-position of the phenyl ring with respect to one of the sulphonic acid groups. The long chain alkyl groups described above may be straight or branched chain alkyl groups. The phenyl ring of the long chain alkylphenyl group may carry substituent groups which increase the acid strength of the sulphonic, disulphonic or phosphonic acids and examples of suitable substituent groups are halogen, especially —F or —Cl, and —$NO_2$.

An especially preferred long chain alkylaryl sulphonic acid is dodecylbenzenesulphonic acid.

The alkyl group represented by $X^1$ or $X^2$ is preferably $C_{1-6}$-alkyl, the halogen group represented by $X^1$ or $X^2$ is preferably —Cl or —Br and the aryl group represented by $X^1$ or $X^2$ is preferably phenyl. In compounds of Formula (1) it is preferred that both $X^1$ and $X^2$ are —H.

The aryl group represented by $W^1$ or $W^2$ is preferably phenyl or substituted phenyl. $W^1$ and $W^2$ may be the same or different. Suitable substituents for the phenyl groups represented by $W^1$ and $W^2$ are preferably selected from alkyl, alkoxy, alkenyl, alkoxyalkoxy, alkoxycarbonylalkoxy, alkoxyalkoxycarbonylalkoxy, alkylcarbonyloxyalkoxy, aryloxy, alkylcarbonyl, alkylsulphonyl, CN-alkoxy, HO-alkoxy, $HO_2C$-alkoxy, halogen, especially chlorine or bromine, hydroxy, nitro, amino, alkylamino, dialkylamino, alkylthio and arylthio. In the substituents for the phenyl groups represented by $W^1$ and $W^2$ it is preferred that the alkyl or alkoxy are $C_{1-4}$-alkyl or $C_{1-4}$-alkoxy, the alkenyl is $C_{3-4}$-alkenyl and the aryl is phenyl.

Where either or both phenyl groups represented by $W^1$ and $W^2$ carry a $HO_2C$-alkoxy substituent this may be esterified with any suitable alcohol.

The compounds of Formula (1) in which Y and Z together form a group of Formula (2) are preferably asymmetric by virtue of differences in the number, type and position of substituents in $W^1$ and $W^2$ and/or by virtue of differences in $X^1$ and $X^2$. Thus, $W^1$ and $W^2$ may be different when $X^1$ and $X^2$ are the same, $W^1$ and $W^2$ may be the same when $X^1$ and $X^2$ are different and $W^1$ and $W^2$ may be different when $X^1$ and $X^2$ are different.

In compounds of Formula (4) R is preferably —H or $C_{1-6}$-alkyl and more preferably —H or $C_{1-4}$-alkyl, and A is preferably —H, —COOR, —OR or phenyl.

Preferred compounds of Formula (1) are those in which $W^1$ is phenyl or is phenyl substituted by a $C_{1-4}$-alkoxy group, Y and Z together are a group of Formula (2) and $W^2$ is phenyl substituted by a $C_{1-4}$-alkoxy-$C_{1-4}$-alkoxycarbonyl$C_{1-4}$-alkoxy group and $X^1$ and $X^2$ are —H.

According to a further feature of the present invention there is provided a process for the preparation of a compound of Formula (1) wherein:

$W^1$ is phenyl or substituted phenyl;
$X^1$ and $X^2$ are as hereinbefore defined;
Y is —H; and
Z is —OH which comprises reacting a compound of Formula (3) wherein:

$X^1$ and $X^2$ are as hereinbefore defined;
Y is —H; and
Z is —OH, with a compound of Formula (4) wherein:
A and R are as hereinbefore defined; and
$W^1$ is phenyl or substituted phenyl, in the presence of an acid catalyst characterised in that the catalyst is a long chain alkyl- or long chain alkylaryl-sulphonic, disulphonic or phosphonic acid.

According to a further feature of the present invention there is provided a process for the preparation of a compound of Formula (1) which comprises reacting a compound of Formula (3) with a compound of Formula (4)
wherein:

$W^1$ is phenyl or substituted phenyl;
$X^1$, $X^2$, A and R are as hereinbefore defined;
Y and Z together form a group of Formula (2); and
$W^2$ is phenyl or substituted phenyl, in the presence of an acid catalyst characterised in that the catalyst is a long chain alkyl- or long chain alkylaryl-sulphonic, disulphonic or phosphonic acid.

According to a further feature of the presence invention there is provided a process for the preparation of a compound of Formula (1) wherein:

$W^1$ is phenyl or substituted phenyl;
$X^1$ and $X^2$ are as hereinbefore defined; and
Y and Z together form a group of Formula (2) wherein $W^2$ is phenyl or substituted phenyl, which comprises reacting a compound of Formula (3) wherein:

$X^1$ and $X^2$ are as hereinbefore defined;
Y is —H; and
Z is —OH, with a first compound of Formula (4) wherein:
A and R are as hereinbefore defined; and
$W^1$is phenyl or substituted phenyl, to form a compound of Formula (1)
wherein:
$W^1$ is phenyl or substituted phenyl;
$W^1$ and $X^2$ are as hereinbefore defined;
Y is —H; and
Z is —OH, which is reacted with a second compound of Formula (4) wherein:
A and R are as hereinbefore defined; and
$W^2$ is phenyl or substituted phenyl, in the presence of an acid catalyst characterised in that the catalyst is a long chain alkyl- or long chain alkylaryl-sulphonic, disulphonic or phosphonic acid.

The process of the present invention may be carried out in an organic liquid, preferably in an organic liquid which does not substantially interfere with the reaction, more preferably in an aromatic hydrocarbon, such as toluene, ethylbenzene or xylene or in a long chain alkyl- or long chain alkylaryl-sulphonic, disulphonic or phosphonic acid such as those described above.

The process of the present invention is preferably carried out at a temperature of from 20° C. to 150° C.

The reaction of a compound of Formula (3), in which Y is —H and Z is —OH and $X^1$ and $X^2$ are as hereinbefore defined, with a compound of Formula (4), in which A, R and $W^3$ are as hereinbefore defined, to form a compound of Formula (1) wherein Y is —H and Z is —OH and $X^1$, $X^2$ and $W^1$ are as hereinbefore defined is preferably carried out at a temperature from 20° C. to 100° C., more preferably from 25° C. to 80° C. and especially from 35° C. to 65° C.

The reaction of a compound of Formula (3), wherein Y and Z together form a group of Formula (2) and $X^1$, $X^2$ and $W^1$ are as hereinbefore defined, with a compound of Formula (4), in which A, R and $W^3$ are as hereinbefore defined, to form a compound of Formula (1) wherein Y and Z together form a group of Formula (2) and $X^1$, $X^2$ and $W^1$ are as hereinbefore defined is preferably carried out at a temperature from 60° C. to 150° C., more preferably from 80° C. to 130° C. and especially from 95° C. to 125° C.

Compounds of Formula (1) in which Y and Z together form a group of Formula (2) may be oxidised to benzodifuranone dyes, the oxidation is preferably carried out at a temperature from 40° to 90° C., more preferably at 50° to 80° C. and especially at 60° to 75° C., using an oxidising agent such as hydrogen peroxide, chloranil or ammonium persulphate, preferably using hydrogen peroxide.

The product may be isolated by removing the organic liquid by distillation, adding a base such as sodium bicarbonate to neutralise any remaining acid, adding water and filtration. Where a long chain alkyl- or alkylaryl-sulphonic, disulphonic or phosphonic acid is used as catalyst and where sodium bicarbonate is used at the end of the reaction to neutralise the catalyst an improved physical form product which can be isolated readily by filtration is obtained, the use of sodium bicarbonate with the present catalyst to improve physical form of the product forms a further feature of the present invention. It is preferred that an excess of sodium bicarbonate of from a 1.05 to 25-fold molar excess, more preferably a 1.1 to 10-fold molar excess over the acid catalyst is used. Recovery of solvents used during the process is aided by the presence of the catalysts of the present invention which tend to prevent the reaction mixture from becoming immobile as solvents are removed. The product may be purified by washing with water and/or organic liquids such as methanol or ethoxyethanol.

The process of the present invention followed by an oxidation as described above may be carried out as a 'one pot' process, i.e. without the need to isolate any of the intermediate stages, for the preparation of benzodifuranone dyes and this forms a further feature of the present invention.

The compounds of Formula (1) are useful intermediates in the preparation of benzodifuranone dyes which are used to dye synthetic fibres such as polyesters.

The invention is further illustrated by the following example:

EXAMPLE 1

Preparation of 3-(4-(n-propoxy)phenyl)-7-(4-(ethoxyethoxycarbonylmethoxy)phenyl)-2,6-dioxo-2,6-dihydrobenzo-[1:2-b, 4:5-b']difuran.

A mixture of hydroquinone (23.1 g), toluene (222 g) and dodecylbenzenesulphonic acid (52.3 g) was heated to 50° C. and 4-n-propoxymandelic acid (42 g) was added in 8 equal portions over 4 hours maintaining the temperature at 50° C. The mixture was stirred for a further 4 hours at 50° C. before adding 4-(carboxymethoxy)mandelic acid (58.8 g) and heating to 110° C. for 4 hours distilling off water of reaction as it was formed. The mixture was cooled to 65° C. and hydrogen peroxide (34.0 g, 130 vol) was added in 10 equal aliquots over 5 hours maintaining the temperature at 65° to 70° C. The temperature of the mixture was maintained at 65° to 70° C. for a further 1 hour before gradually increasing the temperature to 145° C. in order to distil off water and toluene. The reaction mixture was cooled before adding 2-ethoxyethanol (259 g) and heating to 135° C. for 6 hours. The reaction mixture was cooled to 50° C. and sodium bicarbonate (21.0 g) was added before stirring at 50° C. for 1 hour. Water (600 g) was added over 1 hour maintaining the temperature at 50° C. before isolating the product by filtration, washing with ethoxyethanol and/or water and drying to give 3-(4-(n-propoxy)-phenyl)-7-(4-ethoxyethoxycarbonylmethoxy)phenyl)-2,6-dioxo-2,6-dihydrobenzo-[1:2-b, 4:5-b']difuran (60g, 55%).

A further series of experiments were performed to compare the product yield obtained using dodecylbenzenesulphonic acid as catalyst with the product yield obtained using p-toluenesulphonic acid as catalyst. The general procedure of Example 1 was followed using 0.2 g mole (42 g) of 4-n-propoxymandelic acid in each experiment. The dry 100% weight yield of the product in each experiment was calculated from the actual weight yield and the analysed (by liquid chromatography) strength of the product. The experimental details are tabulated in Table 1:

TABLE I

| | Catalyst | Molar Ratio | | Esterifying Alcohol | Dry 100% Weight Yield (%) |
|---|---|---|---|---|---|
| Comparative A | PTSA | n-Proma | 1.0 | Methoxol | 14.9 |
| | | HQ | 1.3 | | |
| | | PTSA | 1.1 | | |
| | | CMMA | 1.3 | | |
| Comparative B | PTSA | n-Proma | 1.0 | Methoxol | 18.8 |
| | | HQ | 1.3 | | |
| | | PTSA | 1.1 | | |
| | | CMMA | 1.3 | | |
| Comparative C | PTSA | n-Proma | 1.0 | Methoxol | 27.0 |
| | | HQ | 1.1 | | |
| | | PTSA | 1.1 | | |
| | | CMMA | 1.3 | | |
| Comparative D | PTSA | n-Proma | 1.0 | Methoxol | 33.3 |
| | | HQ | 1.3 | | |
| | | PTSA | 0.6 | | |
| | | CMMA | 1.3 | | |
| Comparative E | PTSA | n-Proma | 1.0 | Methoxol | 35.5 |
| | | HQ | 1.05 | | |
| | | PTSA | 1.1 | | |
| | | CMMA | 1.3 | | |
| Comparative F | PTSA | n-Proma | 1.0 | Methoxol | 27.0 |
| | | HQ | 1.05 | | |
| | | PTSA | 1.1 | | |
| | | CMMA | 1.3 | | |
| Example 2 | DBSA | n-Proma | 1.0 | Methoxol | 52.0 |
| | | HQ | 1.05 | | |
| | | DBSA | 1.1 | | |
| | | CMMA | 1.3 | | |
| Example 3 | DBSA | n-Proma | 1.0 | Ethoxol | 40.0 |
| | | HQ | 1.05 | | |
| | | DBSA | 0.79 | | |
| | | CMMA | 1.3 | | |
| Example 4 | DBSA | n-Proma | 1.0 | Methoxol | 38.3 |
| | | HQ | 1.05 | | |
| | | DBSA | 0.79 | | |
| | | CMMA | 1.3 | | |
| Example 5 | DBSA | n-Proma | 1.0 | Methoxol | 49.2 |
| | | HQ | 1.1 | | |
| | | DBSA | 0.3 | | |
| | | CMMA | 1.1 | | |
| Example 6 | DBSA | n-Proma | 1.0 | Ethoxol | 47.6 |
| | | HQ | 1.05 | | |
| | | DBSA | 1.0 | | |
| | | CMMA | 1.3 | | |
| Example 7 | DBSA | n-Proma | 1.0 | Ethoxol | 42.0 |
| | | HQ | 1.05 | | |
| | | DBSA | 0.8 | | |
| | | CMMA | 1.3 | | |
| Example 8 | DBSA | n-Proma | 1.0 | Ethoxol | 46.0 |
| | | HQ | 1.05 | | |
| | | DBSA | 0.8 | | |

TABLE I-continued

| Catalyst | Molar Ratio | Esterifying Alcohol | Dry 100% Weight Yield (%) |
|---|---|---|---|
| | CMMA 1.3 | | |

PTSA = P-toluenesulphonic acid
DBSA = dodecylbenzenesulphonic acid
n-Proma = n-propoxymandelic acid
CMMA = 4-(carboxymethoxy)mandelic acid
HQ = hydroquinone
Methoxol = 2-methoxyethanol
Ethoxol = 2-ethoxyethanol Thus, Table 1 clearly indicates that a higher dry 100% weight yield of product is obtained when dodecylbenzenesulphonic acid rather than p-toluenesulphonic acid is used as catalyst.

I claim:

1. A process for the preparation of a compound of Formula (1):

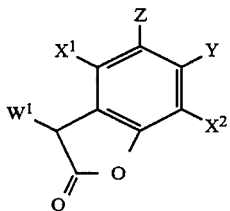

Formula (1)

wherein:
$W^1$ is aryl;
$X^1$ and $X^2$ are each independently selected from —H, —CN, halogen, alkyl, phenyl and —COOH;
Y is —H;
Z is —OH; or
Y and Z together form a group, of Formula (2):

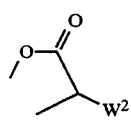

Formula (2)

wherein:
$W^2$ is phenyl or substituted phenyl;
which comprises reacting a compound of Formula (3):

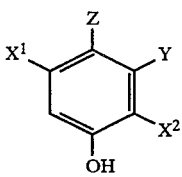

Formula (3)

wherein:
$X^1$, $X^2$, Y and Z are as hereinbefore defined with a compound of Formula (4):

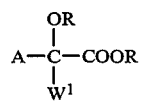

Formula (4)

wherein:
R is —H or -alkyl;
A is selected from —H, —COOR, —OR and phenyl in which R is as hereinbefore defined; and
$W^1$ and $W^2$ are as hereinbefore defined, in the presence of an acid catalyst characterised in that the catalyst is a long chain alkyl- or long chain alkylaryl-sulphonic, disulphonic or phosphonic acid.

2. A process according to claim 1 wherein the catalyst is a $C_{6-25}$-alkyl- or a $C_{6-25}$-alkylaryl-sulphonic, disulphonic or phosphonic acid.

3. A process according to claim 1 wherein the catalyst is a $C_{6-25}$-alkylphenyl-sulphonic, disulphonic or phosphonic acid.

4. A process according to claim 1 wherein the catalyst is a $C_{6-25}$-alkylphenylsulphonic acid.

5. A process according to claim 1 wherein the catalyst is a $C_{6-20}$-alkylphenylsulphonic acid.

6. A process according to claim 1 wherein the catalyst is a $C_{8-16}$-alkylphenylsulphonic acid.

7. A process according to claim 1 wherein the catalyst is dodecylbenzenesulphonic acid.

* * * * *